United States Patent [19]

Palmaz

[11] Patent Number: 4,793,348

[45] Date of Patent: Dec. 27, 1988

[54] BALLOON EXPANDABLE VENA CAVA FILTER TO PREVENT MIGRATION OF LOWER EXTREMITY VENOUS CLOTS INTO THE PULMONARY CIRCULATION

[76] Inventor: Julio C. Palmaz, 12610 Stonehenge, San Antonio, Tex. 78230

[21] Appl. No.: 941,401

[22] Filed: Dec. 15, 1986

[51] Int. Cl.$^4$ .............................................. A61B 17/00
[52] U.S. Cl. .................................................. 128/325
[58] Field of Search ............... 128/325, 1 R, 344, 343, 128/341, 345, 334 R; 210/483, 497.3, 499, 107-109

[56] References Cited

U.S. PATENT DOCUMENTS

| | | | |
|---|---|---|---|
| 2,070,073 | 2/1937 | Walton | 210/499 |
| 2,854,983 | 10/1958 | Baskin | 604/96 |
| 3,540,431 | 11/1970 | Mobin-Uddin | 128/1 R |
| 3,874,388 | 4/1975 | King et al. | 128/334 C |
| 3,882,845 | 5/1975 | Bucalo | 128/1 |
| 3,889,685 | 6/1975 | Miller, Jr. et al. | 128/348 |
| 3,952,747 | 4/1976 | Kimmell, Jr. | 128/1 R |
| 4,183,102 | 1/1980 | Guiset | 3/1.4 |
| 4,483,340 | 11/1984 | Fogarty et al. | 128/344 |
| 4,494,531 | 1/1985 | Gianturco | 128/1 R |
| 4,503,569 | 3/1985 | Dotter | 3/1.4 |
| 4,641,653 | 2/1987 | Rockey | 604/96 |
| 4,643,184 | 2/1987 | Mobin-Uddin | 128/345 |

FOREIGN PATENT DOCUMENTS 0764684 9/1980 U.S.S.R. .
2135585 9/1984 United Kingdom .

OTHER PUBLICATIONS

Peter Eichelter, MD, and Worthington G. Schenk, Jr., MD Buffalo, "Prophylaxis of Pulmonary Embolism", *Arch Surg*-vol. 97, Aug. 1968, pp. 348-356.
Kazi Modin-Uddin, Joe R. Utley, and Lester R. Bryant, "The Inferior Vena Cava Unbrella Filter", *Progress in Cardiovascular Diseases*, vol. XVII, No. 5, (Mar./Apr.), 1975, pp. 391-399.
James W. Pate, M.C., F.A.C.S., David Melvin, M.D., Richard C. Cheek, M.D., "A New Form of Vena Caval Interruption", *Annals of Surgery*, Jun. 1969, pp. 873-880.
James A. Hunter, M.D., Robert Sessions, Richard Buenger, M.D., "Experimental Balloon Obstruction of the Inferior Vena Cava", *Annals of Surgery*, Feb. 1970, pp. 315-320.
Lazar J. Greenfield, M.D., James R. McCurdy, M.D., Phillip P. Brown, M.D., and Ronald C. Elkins, M.D., Oklahoma City, Okla., "A New Intracaval Filter Permitting Continued Flow and Resolution of Emboli", Apr., 1973, *Surgery*, vol. 73, No. 4, pp. 599-606.
John O. F. Roehm, Jr., M.D., Cesare Gianturco, M.D., Merle H. Barth, M.D., Kenneth C. Wright, Ph.D., "Percutaneous Transcatheter Filter for the Inferior Vena Cava", *Radiology*, vol. 150, No. 1, pp. 255-259.
Gunnar Lund, M.D., Joseph A. Rysavy, B. A., Erich Salomonowitz, M.D., Andrew H. Cragg, M.D., Frank Kotula, Wilfrido R. Casteneda-Zuniga, M.D., David W. Hunter, M.D., Carol C. Coleman, M.D., Kurt Amplatz, M.D., "A New Vena Caval Filter for Percutaneous Placement and Retrieval: Experimental Study", *Radiology*, vol. 152, No. 2, Aug., 1984, pp. 369-372.
Rolf W. Gunther, M.D., Hans Schild, M.D., Axel Fries, S. Storkel, M.D., "Vena Caval Filter to Prevent Pulmonary Embolism: Experimental Study", *Radiology*, vol. 156, No. 2, Aug. 1985, pp. 315-320.

(List continued on next page.)

*Primary Examiner*—Stephen C. Pellegrino
*Assistant Examiner*—Denise Whelton
*Attorney, Agent, or Firm*—Pravel, Gambrell, Hewitt, Kimball & Krieger

[57] ABSTRACT

A vena cava filter for preventing migration of venous clots into the pulmonary circulation is disclosed. The filter comprises a tubular body, the wall surface of which is partitioned by a pattern of slots into a latticework to render the tubular body radially expandable; a head piece affixed to the circumference of the distal end of the tubular body; and a plurality of tines affixed in substantially uniform circumferential spacing about the proximal end of the tubular body. The filter is delivered to the inferior vena cava by catheter means. The filter is deployed to an affixed position within the caval lumen by radial expansion to its operative diameter by balloon expansion of a balloon catheter.

32 Claims, 3 Drawing Sheets

OTHER PUBLICATIONS

Morris Simon, M.D., Roy Kaplow, Ph.D, Edwin Salzman, M.D., and David Freiman, M.D., "A Vena Cava Filter Using Thermal Shape Memory Alloy", *Radiology*, 125: pp. 89-94, Oct. 1977.

Aubrey M. Palestrant, M.D., Martin Prince, B. S., Morris Simon, M.D., "Comparative In Vitro Evaluation of the Nitinol Inferior Vena Cava Filter", *Radiology*: 145, pp. 351-355, Nov. 1982.

Andrew Cragg, Gunnar Lund, Erich Salomonowity, Joseph Rysavy, Flavio Castaneda, Wilfrido Castaneda-Zuniga, Kurt Amplatz, "A New Percutaneous Vena Cava Filter", *AJR* 141: pp. 601-604, Sep. 1983.

Donald F. Denny, John J. Cronan, Gary S. Dorfman, Cordell Esplin, "Percutaneous Kimray-Greenfield Filter Placement by Femoral Vein Puncture", *AJR* 145: pp. 827-829, Oct. 1985.

Kazi Mobin-Uddin, MB, BS; Robert McLean; Hooshang Bolooki, MD; and James R. Jude, MD, Coral Gables, Fla., "Caval Interruption for Prevention of Pulmonary Embolism", *Arch Surg*/vol. 99, Dec. 1969.

George E. Cimochowski, M.D., Richard H. Evans, M.D., Christopher K. Zairins, M.D., Chien-Tai Lu, M.D., and Tom R. DeMeester, M.D., Chicago, Ill., "Greenfield Filter Versus Mobin-Uddin Umbrella", *J Thorac Cardiovac Surg*, 79: pp. 358-363, 1980.

Julio C. Palmaz, M.D., Randy R. Sibbitt, M.D., Fermin O. Tio, M.D., Stewart R. Reuter, M.D., J.D., Joseph E. Peters, M.T., and Francisco Garcia, M.D., San Antonio, Texas, *Surgery*, vol. 99, No. 2, pp. 199-205, Feb., 1986, "Expandable Intraluminal Vascular Graft: A Feasibility Study".

Julio C. Palmaz, Randy R. Sibbitt, Stewart R. Reuter, Francisco Garcia, Fermin O. Tio, "Expandable Intrahepatic Portacaval Shunt Stents: Early Experience in the Dog", *AJR*: pp. 821-825, Oct. 1985.

Julio C. Palmaz, M.D., Randy R. Sibbitt, M.D., Stewart R. Reuter, M.D., J. D. Fermin O. Tio, M.D., William J. Rice, M.D., "Expandable Intraluminal Graft: A Preliminary Study", *Radiology*, vol. 156, No. 1, 1985.

Harold Hershenson, Coral Gables, Fla., assignor to Cordis Corporation, Miami, Fla., "Expandable Device for Treating Intravascular Stenosis", *Biomedical Technology*, Jun. 1, 1986, p. 131.

Charles T. Doiter, M.D., "Transluminally-placed Coilspring Endarterial Tube Grafts", *Investigative Radiology*, vol. 4, Sep.-Oct., 1969, pp. 329-331.

Kenneth C. Wright, Ph.D., Sidney Wallace, M.D., Chuslip Charnsangevej, M.D., C. Humberto Carrasco, M.D., Cesare Gianturco, M.D., "Percutaneous Endovascular Stents: An Experimental Evaluation", *Radiology*, vol. 156, No. 1, Jul. 1985, pp. 69-72.

Andrew Cragg, M.D., Gunnar Lund, M.D., Joseph Rysavy, B.A., Flavio Castaneda, M.D., Wilfrido Castaneda-Zuniga, M.D., Kurt Amplatz, M.D., "Nonsurgical Placement of Arterial Endoprostheses: A New Technique Using Nitinol Wire", *Radiology*, vol. 147; pp. 261-263, Apr. 1983.

Charles T. Dotter, M.D., Robert W. Buschnann, P.A.C., Montgomery K. McKinney, Josef Rosch, M.D., "Transluminal Expandable Nitinol Coil Stent Grafting: Preliminary Report", *Radiology* 147: pp. 259-260, Apr. 1983.

D. Maass, Ch. L. Zollikofer, F. Largiader, A. Senning, "Radiological Follow-Up of Transluminally Inserted Vascular Endoprostheses: An Experimental Study Using Expanding Spirals", *Radiology* 1984: 152: pp. 659-663, Sep. 1984.

Andrew H. Cragg, M.D., Gunnar Lund, M.D., Joseph A. Rysavy, B. A., Erich Salomonowitz, M.D., Wilfrido R. Castaneda-Zuniga, M.D., Kurt Amplatz, M.D., "Percutaneous Arterial Grafting", *Radiology*, vol. 150, No. 1, Jan., 1984, pp. 45-49.

Chusilp Charnangevej, M.D., Sidney Wallace, M.D., Kenneth C. Wright, Ph.D., Humberto Carrasco, M.D., Cesare Gianturco, M.D., "Endovascular Stent for Use in Aortic Dissection: An in Vitro Experiment", *Radiology* 1985: vol. 157, pp. 323-324.

Julio C. Palmaz, M.D., Stewart A. Windeler, DDS,Ph.D., Francisco Garcia, MD, Fermin O. Tio, MD, Randy R. Sibbitt, MD, Stewart R. Reuter, MD,JD, "Atherosclerotic Rabbit Aortas: Expandable Intraluminal Grafting", *Radiology* 1986; vol. 160, No. 3, Sep. 1986, pp. 723-726.

BALLOON EXPANDABLE VENA CAVA FILTER TO PREVENT MIGRATION OF LOWER EXTREMITY VENOUS CLOTS INTO THE PULMONARY CIRCULATION

FIELD OF THE INVENTION

This invention relates to a vena cava filter for preventing migration of lower extremity venous clots into the pulmonary circulation. The filter comprises a tubular body, the wall of which is partitioned by a slot pattern into a latticework rendering the tubular body radially expandable; a head piece, having a threaded receiving hole, circumferentially affixed to the distal end of said tubular body; and a plurality of tines affixed in substantially uniform circumferential spacing about the proximal end of said tubular body. In a filter intended for femoral vein introduction into the vena cava the tines are elongated appendages having hooked terminal ends. In a filter intended for jugular vein introduction the tines are short spikes. The filter is delivered to the inferior vena cava by catheter means introduced through a vein sheath positioned in the femoral or jugular vein. After location within the caval lumen the tubular body of the filter is expanded by a balloon catheter contained within the lumen of the filter, thereby rendering the latticework wall surface of the tubular body into a filtering network mesh and affixing the expanded filter within the vena cava. After deployment of the expanded filter within the vena cava the catheter means is withdrawn.

BACKGROUND INFORMATION

It is estimated that in the United States alone pulmonary embolism causes 200,000 deaths a year. The therapy for suspected or impending pulmonary embolism (PE) is anticoagulation drugs or mechanical interruption of the inferior vena cava (IVA). Both treatments are employed for PE prevention in patients who have had one or more past episodes of PE, or in patients who have never experienced PE but who have evidenced venous clots above the knee level. Both groups usually consist of elderly, debilitated, bedridden patients. Complicated surgery, hip fracture, post-partum, sepsis, and extensive trauma are conditions typically complicated by PE.

Prophylactic anticoagulation is usually established on a chronic basis, requiring frequent clinical and laboratory check-ups. Bleeding from acute (initial hospital therapy) and chronic anticoagulation is common and is recognized as the most common treatment-related complication. The health care cost involved in anticoagulation regimens is accordingly high.

As an alternative to anticoagulation, plain intraoperative ligation of the IVC was first reported in 1944. This procedure was usually followed by a highly incapacitating lower extremity swelling caused by venous stasis and did not always prevent subsequent PE which occurred via collateral veins. In an attempt to avoid such complications, partial IVC occlusions were performed by placing transpiercing sutures by a technique called plication, to divide the caval lumen into multiple small channels. Partial restriction of the lumen was also achieved by use of extraluminal serrated clips or extraluminal prostheses to reduce the luminal cross section to a slot shape or simply by placing staples across the cava to reduce the lumen. Loose metal sutures have also been placed across the lumen in order to create a grid or filter plane without restricting the flow. All such methods required major abdominal surgery in patients who were already in critical condition due to the underlying disease or by pulmonary embolism. Among this group the mortality was high, thus restricting such caval interruption procedures to life threatening situations.

The first attempt to arrest embolization by a less invasive method was made by Eichelter in 1968. Peter Eichelter; "Prophylaxis of Pulmonary Embolism". *Arch. Surg.* Vol. 97, pp. 348–356 (1968). His "sieve" consisted of a catheter with a non-detachable distal filtering device, placed through the femoral vein and left in lumen of the IVC temporarily. Soon after Eicheleter's publication, several other devices appeared that were also introduced through a peripheral vein such as the femoral or jugular. These devices were all detachable and designed to remain permanently in the lumen of the IVC.

Mobin-Uddin described an umbrella-like device with radial spokes embedded in a perforated plastic disk. Kazi Mobin-Uddin et al; "The Inferior Vena Cava Umbrella Filter". *Progress in Cardiovascular Diseases,* Vol. 42, No. 5, pp. 391–399 (1975). The Mobin-Uddin device is introduced in a folded fashion inside of a metal capsule and is self-anchoring, after release, by sharp spokes that penetrated the caval wall. A Mobin-Uddin filter has a mandril threaded to the filter to maintain it in straight alignment during delivery. The mandril is unscrewed from the filter after adequate positioning. Experience has demonstrated that Mobin-Uddin umbrella type filters have a high incidence of migration to the heart and causes complete occlusion of the IVC in about half the patients.

In 1969 Pate described a metal clip which was also introduced through a catheter. James W. Pate et al; "A New Form of Vena Cava Interruption". *Annals of Surgery,* Vol. 169, No. 6, pp. 873–880 (1969). That device caused the caval lumen to become reduced to a slot shaped cross section. In 1970 Hunter described a detachable balloon to produce total occlusion of the IVC. James A. Hunter et al; "Experimental Balloon Obstruction of the Inferior Vena Cava". *Annals of Surgery,* Vol. 171, No. 2, pp. 315–320 (1970).

Another device, described by Greenfield, consists of a cone shaped array of 6 wires joined at the apex with recurved hooks at the base. Lazar J. Greenfield et al; "A New Intracaval Filter Permitting Continued Flow and Resolution of Emboli". *Surgery,* Vol. 73, No. 4, pp. 599–606 (1973). Its cartridge design permits trapping of emboli in the apex while allowing continued filtration through the base. The disadvantages of the Greenfield device mainly relate to the progressive separation of the tines toward the base. As the apex fills with clot, larger particles may pass through the base where the spaces are wider; therefore, the filtering ability decreases as the amount of trapped emboli increases. If the Greenfield type filter is deployed in a tilted manner (more than 15 degrees off the axis of the IVC) filtering ability is decreased because the wider spaces between wires is exposed to the central layers of the cava laminar flow which carries the larger emboli. Tilted positioning is not uncommon in this device because it is released by a push rod that ejects the filter out of a capsule. As soon as the tines disengage the capsule they spring open and contact the caval wall. The disengagement may not be simultaneous for all tines, causing the filter to tilt to one side.

All of the remotely introduced filter devices so far described are relatively bulky and have the disadvantage of needing surgical exposure of the jugular or femoral vein in order to be introduced into the cava. It has now become evident that many of the complications related to such filters are due to their misplacement.

Filters made of thermal memory alloys, such as nitinol, have been tried. Although the filter designs varied, the principle of each was the same. Each filter was based on the ability of such an alloy, upon exposure to warm blood, to regain the shape it had prior to annealing. The filter could be introduced in a collapsed fashion through a catheter and would regain its shape in the caval lumen. Unfortunately, the temperature which triggers the change in shape is not critical for such alloys and despite constant infusion of cold saline in the lumen of the introducer tube, premature reshaping often occurs causing jamming of the filter in the catheter.

A different concept was introduced by Roehm. John O.F. Roehm et al; "Percutaneous Transcatheter Filter for the Inferior Vena Cava". *Radiology*, Vol. 150, No. 1, pp. 255-257 (1984). His filtering device was also introduced percutaneously and was termed a "bird's nest filter." It consisted of four strands of fine steel wire, 25 cm long with four fine hooks (2 strands per hook) at both ends. The strands coiled into a mesh inside of the caval lumen and were fixed in place by the hooks. Several migrations of this filter to the heart have occurred and its filtering ability has been questioned since it has been shown that rather large clots may still pass through the irregular pore sizes of the mesh formed by the wires.

Lund in 1984 reported a device similar to the Greenfield filter but made of thinner wire. Gunnar Lund et al; "A New Vena Caval Filter for Percutaneous Placement and Retrieval; Experimental Study". *Radiology*, Vol. 152, No. 2, pp. 369-372 (1984). The Lund device had a threaded hub for accurate positioning and a hook at the distal end for eventual removal. The anchoring tines were straight sharp tips with wire loops limiting penetration in the caval wall. The water hammer effect of totally occlusive emboli suddenly meeting an obstruction may dislodge and cause migration of a Lund type filter which is deployed in cephalic projection by femoral vein introduction. Jugular introduction, which would invert the projection, would stabilize a Lund type filter but its filtering ability would be decreased. The second disadvantage of this device is the short span of the tines limit the range of expansion. The caval lumen measures in the average range of 18-22 mm below the renal veins. Nonetheless, 3-12% of the patient population have IVCs larger than 30 mm. Moreover, the caval diameter may change drastically with cough or strain causing straight tines to become dislodged. A large clot suddenly lodging in a filter, enlarges the diameter of the caval lumen at the site of obstruction, pushing the caval wall away from the tines and causing migration of the filter. This is the main cause of migration of the Mobin-Uddin filter and may affect the Lund filter the same way.

Gunther described another filter made of thin wires that can be introduced through a small venous catheter. Rolf W. Gunther et al; "Vena Caval Filter to Prevent Pulmonary Embolism: Experimental Study". *Radiology*, Vol. 156, No. 2, pp. 315-320 (1985). It consisted of two planes of filtering, a basket and a spider-like portion. The two parts allow it to self-center in the lumen. Its anchoring mechanism is similar to the Lund filter, and therefore subject to the same problems.

Despite the medical community's awareness of the morbidity, high cost and liability involved in anticoagulation as a treatment for the prevention of PE, the alternate treatment -- use of filters -- has not yet gained wide popularity. Most of the physicians arguing against filters base their preference for anticoagulation on the rather large list of complications published for the caval filter designs known to date. Although many of such complications may be avoided in the future by better use of fluoroscopy; nevertheless, migration and ineffective filtering remain as the two primary problems detracting from wider use of known filter devices.

If a vena cava filter having a higher level of acceptance can be developed, not only will the filter be used in life threatening situations (previous life-threatening episode of PE, multiple small episodes of PE leading to progressive occlusion of the pulmonary arteries and pulmonary hypertension, documented clot in large veins) but also in patients without a history of deep venous thrombosis or PE, yet who suffer from any of the following conditions; cancer victims on chemotherapy, particularly if old and/or debilitated, candidates for major surgery and anticipated slow recovery, elderly patients undergoing total hip replacement, complicated postpartum, severe burns, renal vein thrombosis, crushing pelvic fracture or other severe forms of trauma. In such conditions a patient's demise is frequently related to fatal PE, and accounts for most of the estimated 200,000 PE deaths per year which occur in the United States.

SUMMARY OF THE INVENTION

The vena cava filter of the present invention comprises a tubular body partitioned by a pattern of slots into a latticework wall surface to render the tubular body radially expandable; a head piece, with a threaded receiving bore in its apex, secured about the circumference of the distal end of the tubular body; and a plurality of tines secured to the proximal end of the tubular body in substantially uniform circumferential spacing. In a filter intended for femoral vein introduction into the vena cava the tines are elongated appendages having hooked terminal ends. In a filter intended for jugular vein introduction the tines are short spikes.

The filter of femoral vein introduction design, upon radial expansion, provides a cartridge design with uniform pore size from top to base to avoid loss of filtering capacity as the filter cartridge fills with trapped emboli. The hook ends of the elongated tine appendages angulate radially outwardly to contact and provide sure anchorage of the expanded filter within the luminal wall of the vena cava. A filter of jugular vein introduction design provides, upon radial expansion, a screen design of uniform pore size from top to base to provide uniform screening of emboli in the blood flow along the caval wall. The short spike tines are positioned by expansion of the proximal end of the tubular body into expansion contact with the caval wall to contact and anchor into the caval wall.

The radial expansibility of either filter embodiment not only promotes secure anchoring within the lumen of the vena cava but also provides a wide variability of the base diameter of the filter permitting its adaptation to all caval sizes. The filter is radially flexible after deployment in the vena cava allowing the implanted filter to adapt to the varying diameters of the cava induced under different physiological conditions. Since the nonexpanded diameter of the filter is small it is suitable for percutareous placement by suitable catheter means.

DESCRIPTION OF THE PREFERRED EMBODIMENTS

The vena cava filter of the invention as designed for femoral vein introduction comprises a thin wall tubular body having a slotted pattern formed in the wall surface to render the tubular wall surface radially expandable; a head piece securely affixed about the circumference of the distal end of the tubular body; and a plurality of tines, having recurved hook ends, affixed at substantial uniform spacing about the circumference of the proximal end of the tubular body. Measured from the apex of the head piece to the terminal ends of the tines, the vena cava filter may range in length from about 20 to about 75 mm, with a preferred length of about 45 mm. The unexpandable diameter of the tubular body may range from about 3 to about 8 mm, with an unexpanded diameter of about 6 mm preferred. The length of the tubular body from distal to proximal end may range from about 10 to about 40 mm. For a filter of preferred 45 mm length a tubular body length of about 26 mm, a head piece length of about 4 mm, and a tine length of about 15 mm are preferred.

Figure 1A:
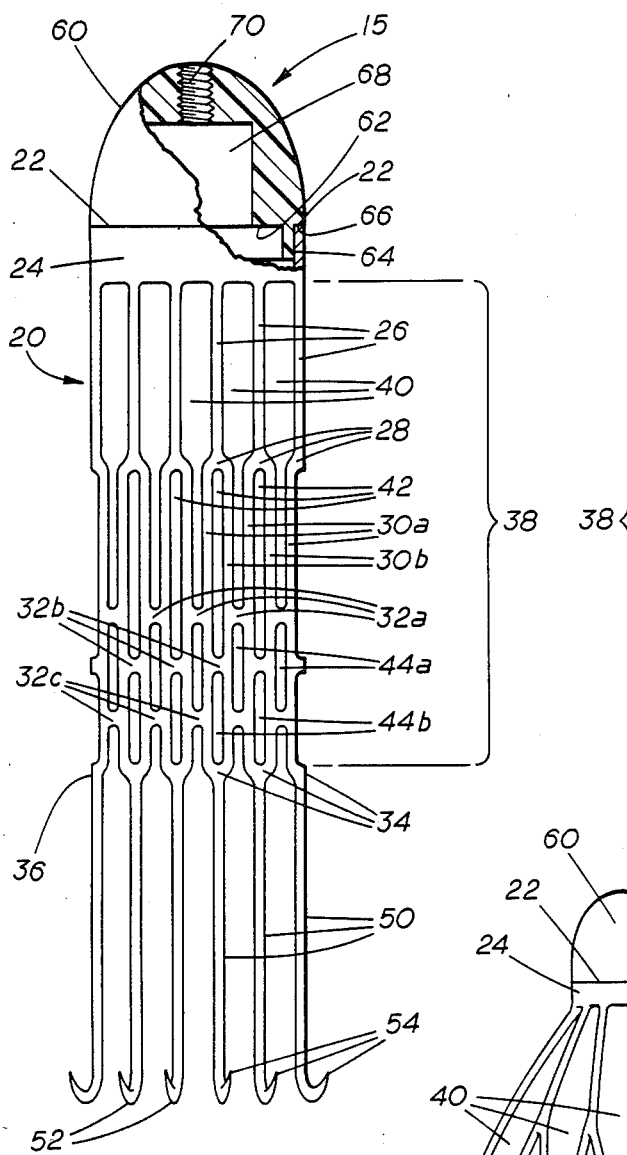
FIG. 1A illustrates in side view a nonexpanded vena cava filter of the invention designed for femoral vein introduction, with the head piece shown in partial section.

FIG. 1A illustrates an embodiment of a vena cava filter 15 of the invention designed for femoral vein introduction. Filter 15 comprises a head piece 60 affixed to distal end 22 of a radially expansible tubular body member 20 which at its proximal end 36 carries in uniform circumferential spacing depending tines 50 having recurved hook ends 54.

Tubular body 20 comprises a distal end 22, a proximal end 36 and a latticework wall surface 38 disposed therebetween. The tubular body 20 of filter 15 has a wall thickness of from about 0.1 to about 1.0 mm; and preferably about 0.3 mm. The tubular body 20 may be made of any suitable material which is compatible with the body parts and fluids with which it may be placed in contact, and possesses the strength and plasticity to permit radial expansion of the latticework wall surface 38 of the tubular body 20. The tubular body 20 may for instance be made of silver, tantalum, stainless steel, gold, titanium or a suitable biocompatible polymer which possess the requisite properties of strength and plasticity as previously described. Stainless steel is the preferred material for construction of the tubular body 20.

Between the distal 22 and proximal 36 ends of tubular body 20 a series of primary slots 40, major secondary slots 42, and minor secondary slots 44a and 44b are formed which partition the tubular wall into a latticework wall surface 38. The latticework wall surface 38 is partially defined by a series of longitudinal rib members 26 depending in a substantially uniform circumferential spacing from a receiving collar 24 at distal end 22 of the tubular body 20. At branch points 28 each longitudinal rib member 26 diverges into a pair of intermediate longitudinal rib members, 30a and 30b. The pairs of intermediate longitudinal rib member 30a and 30b, define the tubular body 20 wall surface between branch point 28 and the proximal end 36 which is delineated by return points 34 at which intermediate longitudinal rib members 30a and 30b of a pair converge to rejoin one to another.

Transverse rib members 32a, 32b, and 32c are disposed in the tubular wall surface between branch points 28 and return point 34 in descending alternation between intermediate longitudinal rib members 30a and 30b to interconnect and intraconnect intermediate longitudinal rib member pairs, thereby providing a latticework wall surface 38. As illustrated in FIG. 1, transverse rib members 32a interconnect intermediate longitudinal rib pairs (rib 30b of one pair to rib 30a of an adjacent pair), transverse rib members 32b intraconnect the members of a pair of longitudinal rib member (rib 30a to rib 30b of the same pair), and transverse rib members 32c interconnect intermediate longitudinal rib member pairs (rib 30b of one pair to rib 30a of an adjacent pair).

Although the number of longitudinal rib members 26 into which the tubular body 20 is partitioned by primary slots 40 may range between about ten to about sixteen; for a filter having an unexpanded diameter of 6 mm, it is preferred to partition the tubular wall surface into from about twelve to about sixteen longitudinal rib members 26. This provides a body having respectively from about twenty-four to about thirty-two intermediate rib members 30a and 30b, with the body being terminated with respectively from about twelve to about sixteen tines 50.

For a filter of a preferred 6 mm unexpanded diameter which is partitioned into twelve longitudinal rib members; the width of all rib members, tines and the slots between intermediate rib members is preferably about 0.4 mm; for a sixteen longitudinal rib member filter the width preferred is about 0.3 mm. The preferred length of the longitudinal rib members 26 is 10 mm, of the major secondary slots 40 is 10 mm, of the minor secondary slots 44a and 44b is 5 mm, and of the tines 50 is 15 mm. For preferred dimensions as above described, the tubular body of a twelve longitudinal rib member filter could have an expanded diameter of 28.5 mm; a sixteen longitudinal rib member filter could have an expanded diameter of 37.5 mm.

Tines 50 are affixed at a substantially uniform circumferential spacing to the proximal end 36 of tubular body 20. As illustrated in FIG. 1, tines 50 may be integrally formed with tubular body 20 and depend from return points 34. When tines 50 are integrally formed of the material comprising tubular body 20 the tines will be of the same material. However, if desired, tines 50 may be separately made and affixed by welding, soldering or otherwise affixing to the proximal end 36 of the tube body 20. In either event, the terminal ends 52 of tines 50 are curved to form recurved hooks 54, preferably with about a 0.5 mm radius of curvature to insure that the hooks 54 so formed are incapable of through penetration of the vena cava wall. Whether integrally formed with the tubular body 20 or separately made then affixed, the tines 50 are positioned about the tubular body 20 such that the recurved hook ends 54 project radially outwardly from the tubular body 20.

The filter head piece 60 comprises a hollow conical, semi-spherical or dome shaped body having a base 62 to which is integrally formed or securely affixed a mounting ring 64 of slightly smaller outer diameter than that of base 62. The diameter difference defines an abutment shoulder 66 between base 62 and ring 64 by which head piece 60 may be brought into abutting contact with the distal end 22 of tubular body 20. The hollow or collecting cavity 68 of the head piece 60 communicates with a threaded bore 70 positioned in the apex and concentric to the axis of head piece 60.

Head piece 60 may be made of any metallic or polymeric material which is biocompatible with the body parts and fluids to be contacted by filter 15. Head piece 60 is mounted to the distal end 22 of tubular body 20 by positioning mounting ring 64 within the receiving collar 24 of the tubular body 20 until abutment of shoulder 66 with distal end 22 occurs. Head piece 60 is securely affixed to distal end 22 by gluing ring 64 within receiving collar 24 with a biocompatible glue (especially if head and tubular body are not each of a metallic composition), or by welding, soldering or braising along the junction line between head 60 and body 20 (especially if head and tubular body are both of metallic composition).

Head piece 60 may be made by injection molding or casting of a polymeric material or by machining from a metallic or plastic body. Tubular body member 20 may be fabricated by joining the requisite collar element 24 to the requisite rib member structures by welding, braising or soldering after which rib pairs 30a and 30b are cross soldered to form transverse rib members 32a, 32b and 32c. Preferably, tubular body 20 is integrally fabricated from a thin walled tube by etching of the requisite slot pattern into the tube wall by a conventional etching process, such as electromechanical etching, laser etching, acid etching or water jet blasting. When fabricated by an etching process it is preferred to prepare tines 50 integral with the tubular body 20 by the etching process.

Figure 2:
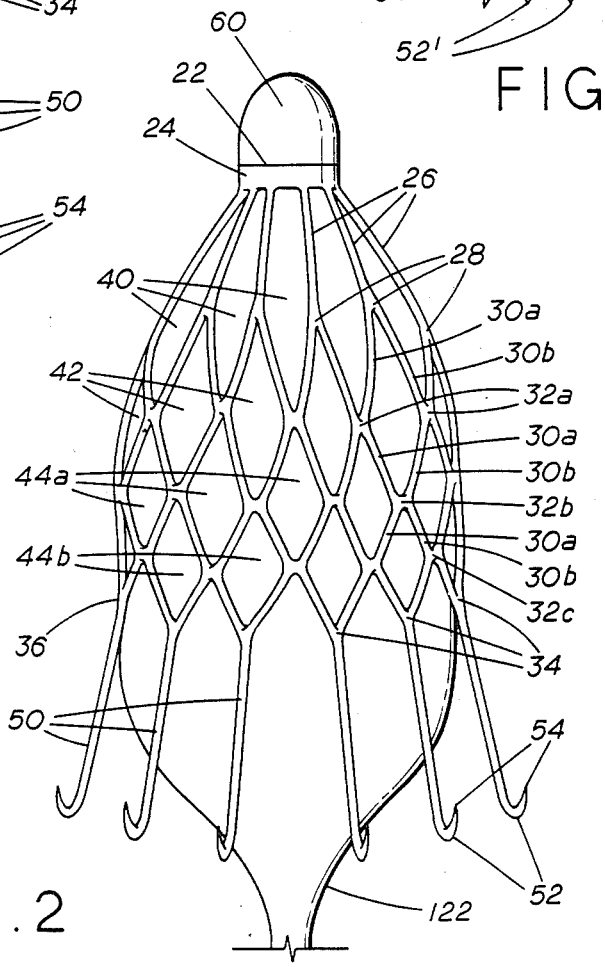
FIG. 2 illustrates an expanded state filter of FIG. 1A as produced by balloon inflation.

The assembly of head piece 60, latticework tubular body member 20 and tines 50 comprises the vena cava filter 15 of the invention. As illustrated by FIG. 2, application of radially outward pressure to the lumen of tubular body 20 expands filter 15 to a substantially greater diameter than that of its initial state. Radially outward expansion of the tubular body 20 of filter 15 opens the slots 40, 42, 44a and 44b forming the latticework wall surface 38 into a diamond shaped filtering mesh network. The expansion of body member 20 also causes tines 50 to project angularly outwardly from filter body 20 to position the hook ends 54 of tines 50 to anchor into the cava wall to secure filter 15 in place upon deployment. By reason of the strength and plasticity of the material comprising the tubular body 20, filter 15 maintains the expanded diameter after removal of the radial expansion force. The length of minor secondary slots 44a and 44b of the tubular body 20 control the maximum pore size to which filter 15 may be opened by radial outward expansion. For instance, for tubular body of 6 mm unexpanded diameter having minor secondary slots of 5 mm length, the maximum pore size to which the filter may be expanded is about 7.07 mm.

Often times femoral vein introduction of a vena cava filter is contraindicated by a condition of the subject. Hence, for subjects known to have venous clots above knee level or exhibiting lower extremity swelling above knee level, catheter introduction of a vena cava filter through the femoral vein is contraindicated. A further contraindication would be the existence of a wound, surgical or otherwise, in the area wherein the femoral vein would be accessed. Such a wound could cause possible contamination of a filter introduced through the femoral vein.

Figure 1B:
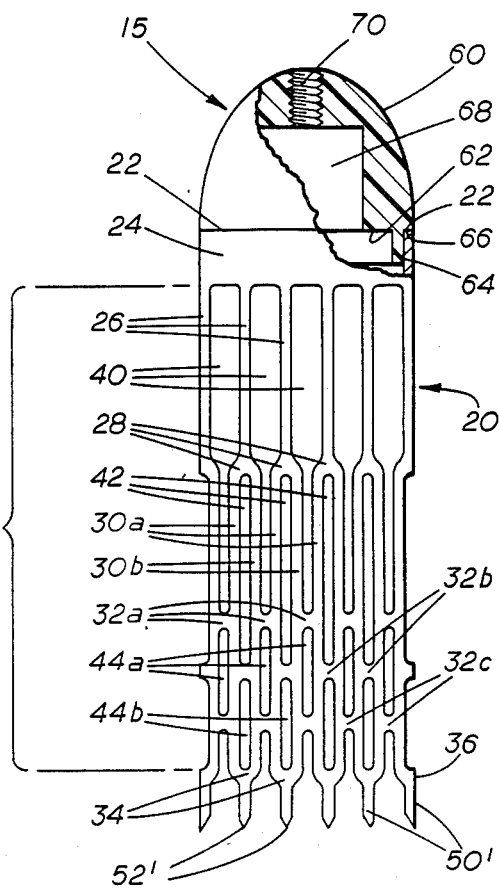
FIG. 1B illustrates in side view a vena cava filter of the invention designed for jugular vein introduction.

FIG. 1B illustrates an embodiment of the vena cava filter designed for jugular vein introduction. In this embodiment, the head piece 60 and tubular body 20 are similar to that of the filter embodiment designed for femoral vein introduction, and discussion thereof will not be repeated. In the jugular vein introduction embodiment only the tines 50' are different. Tines 50' are relatively short appendages having spike terminal ends 52'. This embodiment of the filter is deployed within the vena cava by expansion of the tubular body 20 to a diameter wherein the proximal end 36 compresses into and slightly expands the cross sectional area of the caval lumen. Tines 50' are thus expanded into a tight compression fit with the cava luminal wall and spike ends 52' penetrate into and anchor in the luminal wall. Since proximal end 36 is expandable into a tight compression fit to slightly expand the luminal wall it is secured against dislodgement by momentary physiological stress conditions that may otherwise temporarily enlarge the caval diameter.

Figure 3:
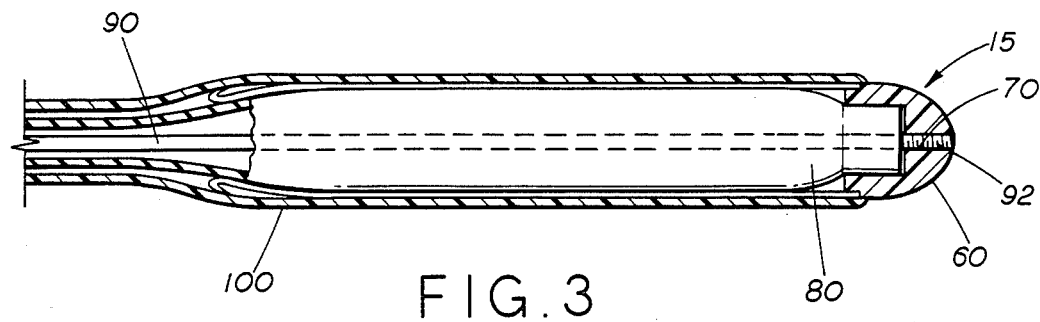
FIG. 3 illustrates in cross section a folded balloon of a balloon catheter inside a nonexpanded filter, with the filter and balloon assembly contained in a delivery capsule.

FIG. 3, illustrated in cross section, shows a filter 15 of the invention as assembled into a delivery capsule for delivery to the vena cava by catheterization procedures. The assembly comprises a folded balloon 80 housed in the lumen of filter 15. The central lumen of the balloon catheter carries a mandril 90 having a threaded end 92 which is screw connected to the threaded bore 70 of head piece 60 of filter 15. Disposed about the exterior of filter 15 is a tight fitting sheath or delivery capsule 100. The delivery capsule has a proximal end (not illustrated) which is a conventional connector for attachment to the end of a catheter as illustrated by FIG. 4.

Figure 4:
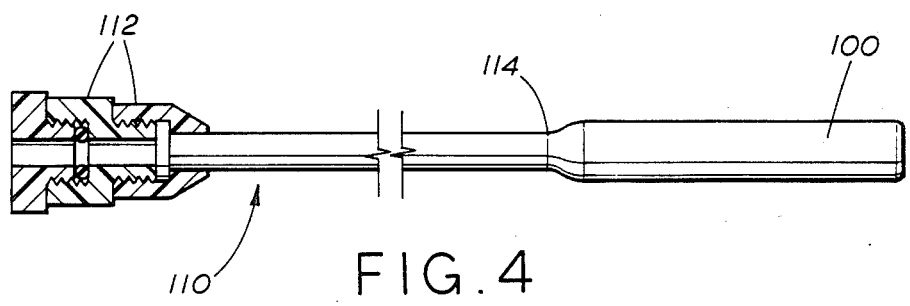
FIG. 4 illustrates a delivery capsule, as in FIG. 3, attached to a delivery catheter; the proximal end of the delivery catheter having a compression valve fitting.

FIG. 4 illustrates a delivery catheter 110 having a proximal end fitted with a compression valve 112 and the delivery capsule 100 connected to the catheter distal end 114.

Figure 5:
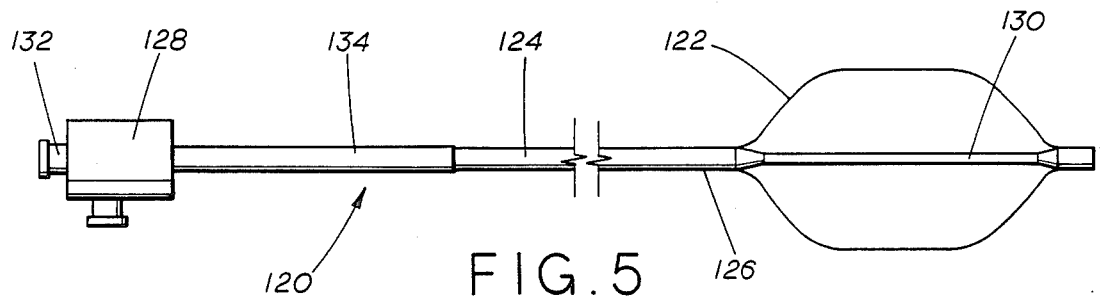
FIG. 5 illustrates a balloon catheter having its proximal shaft covered with metal tubing for smooth sliding through a compression valve.
Figure 6:
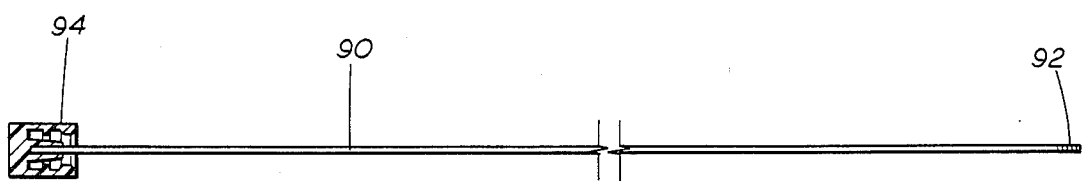
FIG. 6 illustrates a threaded mandril for insertion through the balloon catheter main lumen screw connection into the filter head piece.

FIG. 5 illustrates a balloon catheter 120 with a balloon 122 in expanded state. The shaft unit 124 of catheter 120 comprises axially concentric or parallel tubes. The exterior tube 126 communicates with valve 128 through which a fluid or gas is supplied to the lumen of the balloon for expansion. The interior tube 130 communicates with fitting 132 and is the conduit through which threaded mandril 90, as illustrated by FIG. 6, passes to screw connect to head piece 60 of filter 15. The proximal end of shaft unit 124 is covered with a metal tubing 134 for smooth sliding through compression valve 112 of the delivery catheter 110 of FIG. 4.

FIG. 6 illustrates mandril 90 with a threaded distal end 92 and a proximal end connection fitting 94 for securing mandril 90 within the interior tube 130 of balloon catheter 120 by connection with fitting 132 of balloon catheter 120.

Figure 7:
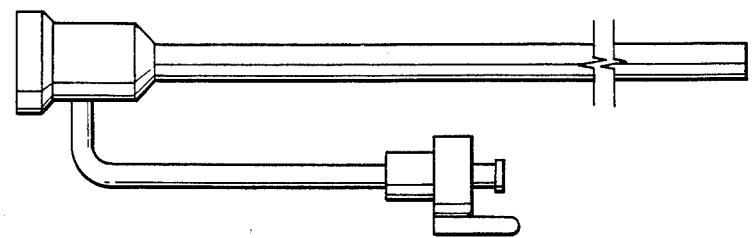
FIG. 7 illustrates an introducer sheath.
Figure 8:
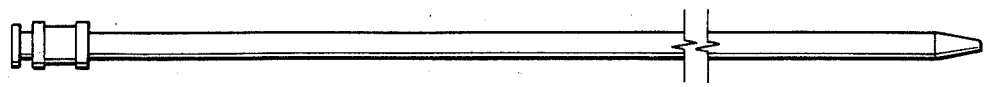
FIG. 8 illustrates a dilator.

FIG. 7 illustrates an introducer sheath and FIG. 8 illustrates a dilator. The dilator is inserted and coaxially mounted inside of the introducer sheath. An incision is made to expose the femoral or jugular vein, as the case may be, and the sheath-dilator assembly is introduced into the vein after which the dilator is withdrawn from the sheath. The delivery system catheter, as illustrated in FIG. 9, is introduced within the vena cava by passage through the introducer sheath.

Figure 9:
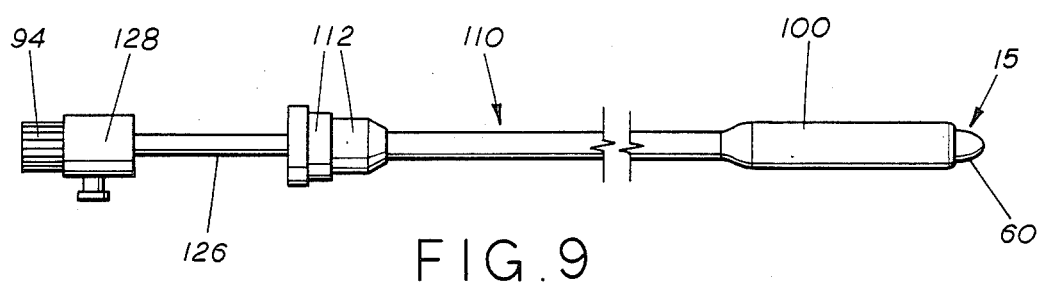
FIG. 9 illustrates a complete delivery system with a filter of the invention in a delivery capsule.
Figure 10:
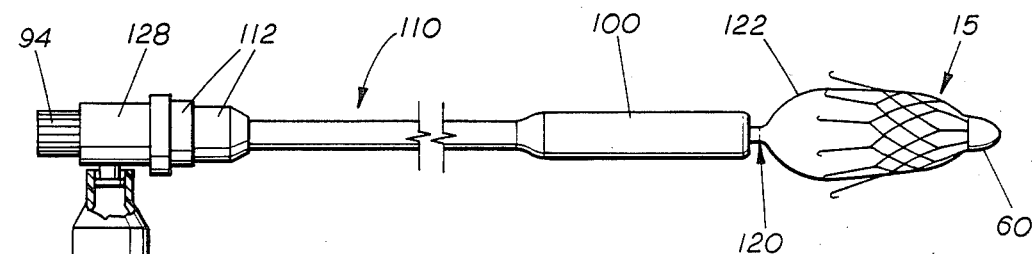
FIG. 10 illustrates the filter delivery system after the delivery capsule has been drawn back to expose the filter and the balloon of the balloon catheter has been inflated to expand the filter.

FIG. 9 illustrates a complete delivery system with a filter 15 in place within delivery capsule 100. The complete delivery system comprises a balloon catheter 120 coaxially mounted with the lumen of a delivery catheter 110 such that balloon 122 is contained within the lumen of an nonexpanded filter 15, the exterior of the filter is covered by delivery capsule 100 and mandril 90 is secured to head piece 60 to secure filter 15 in position about balloon 122. FIG. 10 illustrates the status of the delivery system with the delivery capsule catheter 110 drawn back to expose filter 15 from delivery capsule 100 for expansion of filter 15 by balloon catheter 120. Mandril 90 is still screw connected to the head piece 60 of filter 15, as indicated by the presence of the mandril proximal end connector 94 secured about fitting 132 of the inner conduit 130 of balloon catheter 120.

The filter of the invention is delivered in an unexpanded state to the vena cava as an assembly contained in a delivery capsule attached to a catheter. The lumen of the filter houses a folded balloon which is slightly longer than the filter itself. The central lumen of the balloon catheter contains a mandril with a threaded end which is screw connected into the threaded receiving bore of the head piece of the filter. The assembly is contained in a delivery capsule which is attached to the end of a catheter. The capsule fits tightly over the filter and the filter head piece protrudes beyond the capsule. A vein sheath is located within the femoral or jugular vein of a subject. The loaded capsule is introduced through a vein sheath with a check-valve, after removal of the corresponding dilator.

After the capsule reaches the desired cava position the shaft of the balloon catheter is held in place while the capsule catheter is drawn back, exposing the collapsed filter wtih the folded balloon inside. Inflation of the balloon expands the slots of the filter tube body into diamond shape spaces and therefore the filter tube diameter increases. The screwed on mandril keeps the filter tube from sliding off the balloon during inflation. Upon expansion the tines at the proximal end of the filter tube project radially, angulating outwardly from their point of attachment to the filter tube. The tines are forced into contact with the caval wall both by overall diameter enlargement of the filter tube and by outward angulation. Upon contact, the terminal ends of the tines, whether hook ends as in a filter for femoral vein introduction or spikes as in a filter for jugular vein introduction, securely engage the caval wall without through penetration since the tine terminal ends are dimensioned to limit that penetration. After engagement, the tines remain lightly spring-loaded, providing flexibility to changes in diameter and shape of the IVC at the site of deployment. The degree of elasticity of the tines is a function of the inflated diameter of the balloon in relationship to the caval diameter, the dimensions of the tines and the elastic limit of the metal. After balloon deflation, the mandril is unscrewed from the filter head piece and the balloon collapsed and withdrawn into the capsule. The latter is in turn pulled back out through the vein sheath. A diagnostic angiographic catheter can be introduced through the check-valve of the vein sheath for contrast injections into the caval lumen to confirm adequate placement and patency of the filter. Finally, the sheath is removed and the puncture site manually compressed until hemostasis occurs.

Although the invention has been illustrated and described with regard to its preferred embodiments, one of ordinary skill in the art may appreciate changes and modifications that may be made thereto which do not depart from the scope and spirit of the invention described above and claimed hereafter.

I claim:

1. A vena cava filter for preventing migration of lower extremity venous clots into pulmonary circulation, comprising:
    a tubular body having a distal end, a proximal end and therebetween means for rendering the tubular body radially expandable into a plastically deformed shape, said means comprising a wall surface partitioned by a pattern of slots into a latticework;
    a head piece circumferentially affixed to the distal end of said tubular body; and
    a plurality of tines affixed about the proximal end of said tubular body.

2. The filter of claim 1 wherein the head piece includes a collecting cavity.

3. The vena cava filter of claim 2, wherein the tines are elongated appendages having hooked terminal ends.

4. The vena cava filter of claim 3, wherein the tines are affixed at their ends opposite said terminal ends in substantially uniform circumferential spacing to the proximal end of said tubular body.

5. The vena cava filter of claim 4, wherein the tines have curved hook terminal ends.

6. The filter of claim 3 wherein the tubular body is a metallic material.

7. The filter of claim 6 wherein the pattern of slots by which the tubular body wall surface is partitioned into a latticework are formed by an etching process.

8. The filter of claim 7 wherein the slot pattern is formed by electromechanical etching.

9. The filter of claim 6 wherein the tubular body is stainless steel.

10. The filter of claim 9 wherein the wall surface of the tubular body is of a thickness of from about 0.1 to about 1.0 mm.

11. The filter of claim 10 wherein the tubular body has a length from its distal to proximal ends of from about 10 to about 40 mm.

12. The filter of claim 10 wherein the tubular body has an unexpanded diameter of from about 3 to about 8 mm.

13. The vena cava filter of claim 12, wherein the tines have a length of from about 10 to about 20 mm.

14. The filter of claim 1 wherein the latticework is defined by:
   a plurality of longitudinal rib members depending in substantially uniform circumferential spacing from a receiving collar at the distal end of the tubular body, each of said longitudinal rib members diverging at a branch point to form pairs of intermediate longitudinal rib members which extend to a return point at which each of the pairs of the intermediate longitudinal rib members converge to join one to another of a pair to define the proximal end of said tubular body, and
   transverse rib members disposed in descending alteration between the intermediate longitudinal rib members to interconnect and intraconnect the intermediate longitudinal rib member pairs.

15. The filter of claim 14, wherein the tubular body has an unexpanded diameter of about 6 mm, a length from the distal to proximal end of about 26 mm, the longitudinal rib members have a length of about 10 mm, and the transverse rib members intraconnecting a longitudinal rib member pair are disposed at a longitudinal distance one from another of about 5 mm, and the transverse rib members interconnecting adjacent pairs of intermediate longitudinal rib members are disposed at a longitudinal distance one from another of about 5 mm.

16. The filter of claim 13, wherein the tines are elongated appendages having a length of about 15 mm and a hook end extension length of about 0.5 mm.

17. The vena cava filter of claim 2, wherein the tines are short appendages having spiked terminal ends.

18. The vena cava filter of claim 14, wherein the tines are short appendages having spiked terminal ends.

19. The vena cava filter of claim 18, wherein the tines have a length of from about 0.5 to about 2 mm.

20. A method for deploying a vena cava filter within the inferior vena cava of a body, comprising the steps of:
   disposing upon a catheter a vena cava filter comprising a head piece attached to a distal end of an expandable tubular body and a plurality of anchoring tines attached in uniform circumferential spacing about a proximal end of said tubular body;
   inserting the filter carrying catheter within the inferior vena cava; and
   expanding a portion of the catheter associated with the expandable tubular body of the filter to radially outwardly expand the tubular body to its operative filtering diameter and securely contact and affix the anchoring tines of said filter to the inferior vena cava luminal wall.

21. The method of claim 20, further including the steps of:
   collapsing the portion of the catheter associated with the expandable tubular body of the filter, and removing the catheter from the body passageway.

22. A vascular filter comprising a hollow tubular latticework body having a distal end with a head piece affixed thereto and a proximal end with a plurality of tines affixed thereto, wherein the tubular latticework body defines means for rendering the filter plastically expandable, said means comprising:
   a plurality of longitudinal rib members depending in substantially uniform circumferential spacing from a receiving collar at the distal end of the tubular body, each of said longitudinal rib members diverging at a branch point to form pairs of intermediate longitudinal rib members which extned to a return point at which each of the pairs of the intermediate longitudinal rib members converge to join one to another of a pair to define the proximal end of said tubular body, and
   transverse rib members disposed in descending alteration between the intermediate longitudinal rib members to interconnect and intraconnect the intermediate longitudinal rib member pairs.

23. The vascular filter of claim 22, wherein the tines are elongate appendages having hooked terminal ends and are affixed by their other ends in substantially uniform circumferential spacing about the proximal end of said tubular body.

24. A filter delivery system, comprising:
   a filter comprising an expandable tubular latticework body having a distal and a proximal end, a head piece having a threaded bore affixed to said distal end and a plurality of tines affixed to said proximal end;
   a catheter having a means for expansion associated therewith disposed within the tubular body of said filter, said catheter with associated means for expansion having a central lumen; and
   a mandril disposed within the lumen of said catheter and associated expansion means and screw connected with the threaded bore of the head piece of said filter to secure said filter in place on said catheter with associated expansion means.

25. The filter delivery system of claim 24, wherein said catheter with associated expansion means is a balloon dilatation catheter.

26. The filter delivery system of claim 25, further comprising:
   a delivery catheter having a central lumen within which said balloon dilatation catheter is disposed and a delivery capsule within which said filter is disposed, said delivery capsule being affixed to said delivery catheter.

27. A vena cava filter comprising:
   a head piece including a collecting cavity for collecting venous clots to prevent their passage beyond the filter; and
   an intermediate latticework portion secured to said head piece and including:
   circumferentially spaced primary slots providing a primary passageway for unclotted venous fluid passage about said head piece; and
   circumferentially spaced secondary slots providing a secondary passageway for unclotted venous fluid passage about said head piece such that said latticework portion is capable of being radially expanded into a plastically deformed shape; and
   means secured to said latticework portion for securing said filter within a vena cava.

28. The filter of claim 27, further comprising means for limiting the radially outward expandability of said latticework portion.

29. The filter of claim 28, wherein said radial expansion limiting means includes said secondary slots being sized to limit the radial expandability of said latticework portion to a predetermined radial dimension.

30. The filter of claim 27, wherein said latticework portion is comprised of a material which is plastically deformable when subjected to radially outward forces from within said latticework portion.

31. The vena cava filter of claim 29, wherein:

said primary slots include a plurality of slots of substantially equal size arranged in at least one circumferential row adjacent said head piece; and said secondary slots include a plurality of slots of substantially equal size smaller than the size of said primary slots and arranged in at least one circumferential row adjacent said filter securing means.

32. The vena cava filter of claim 27, wherein said filter securing means includes a plurality of tines.

* * * * *